US008108225B2

(12) United States Patent
Logue

(10) Patent No.: US 8,108,225 B2
(45) Date of Patent: Jan. 31, 2012

(54) METHOD, SYSTEM, AND SOFTWARE FOR ANALYSIS OF A BILLING PROCESS

(76) Inventor: Joan Logue, Longwood, FL (US)

(*) Notice: Subject to any disclaimer, the term of this patent is extended or adjusted under 35 U.S.C. 154(b) by 2303 days.

(21) Appl. No.: 11/013,927

(22) Filed: Dec. 17, 2004

(65) Prior Publication Data

US 2005/0152520 A1    Jul. 14, 2005

Related U.S. Application Data

(60) Provisional application No. 60/529,732, filed on Dec. 17, 2003.

(51) Int. Cl.
*G06Q 40/00* (2006.01)
(52) U.S. Cl. ......................................................... 705/2
(58) Field of Classification Search ........................ 705/2
See application file for complete search history.

(56) References Cited

U.S. PATENT DOCUMENTS

| | | | |
|---|---|---|---|
| 6,464,136 B2* | 10/2002 | Walsh | 235/380 |
| 6,526,125 B1* | 2/2003 | Lindsay et al. | 379/45 |
| 6,637,649 B2* | 10/2003 | Walsh | 235/380 |
| 6,655,583 B2* | 12/2003 | Walsh et al. | 235/380 |
| 6,826,536 B1* | 11/2004 | Forman | 705/4 |

* cited by examiner

*Primary Examiner* — Robert Morgan
*Assistant Examiner* — Reginald R Reyes
(74) *Attorney, Agent, or Firm* — Foley & Lardner LLP

(57) ABSTRACT

A method, system, and software for analyzing third party payments for provider service includes processing third party payment information data and processing provider services billing data provided to the third party to request payment. The method automatically validates provider services billing data against other provider services data and generating a report listing discrepancies between the third party payment information data, the provider services billing data, and the other provider services data.

17 Claims, 14 Drawing Sheets

MBA Final Report $\,500$

| Physician | Patient Status | Medical RecNum | Patient Name | Encounter | Encounter Date | Phys Diagnosis | Phys Ordered | Lab Tests Resulted | Collection Date | Lab Description | Finance Description | CPT Description |
|---|---|---|---|---|---|---|---|---|---|---|---|---|
| Brown | ER | 431598 | Appleton, Angela | 74299602 | 01/03/2003 | Urinary Tract Infection | BMP | True | 01/03/2003 | (1) Basic Metabolic Pane (2) Chem 7 (40111067) | BASIC METABOLIC PANEL (CPT=80048) | Base metabolic panel. This panel must include the following: Calcium (82310) |
| Brown | ER | 431598 | Appleton, Angela | 74299602 | 01/03/203 | Urinary Tract Infection | CBC | True | 01/03/2003 | (1) Urinalysis w/Microsc (2) Urine with Micro PAT (40112561) | URINALYSIS WITH MICROSCOPIC (CPT=81001) | automated with microscopy |
| Brown | ER | 431508 | Appleton, Angela | 74299602 | 01/03/2003 | Urinary Tract Infection | UA | True | 01/03/2003 | (1) Hemogram/pt/dif (2) CBCDF (40121004) | CBC/DIFF/PLT (CPT=85025) | complete (CBC), automated (Hgb, Hct, RBC, WBC, and platelet count) |
| Brown | ER | 431598 | Appleton, Angela | 74299602 | 01/03/2003 | Urinary Tract Infection | Urine culture | True | 01/03/2003 | (1) Urine Culture-Clean (2) Urine Culture-Cath (40141930) | CULTURE URINE (CPT=87086) | Urine Culture-clean Culture, bacterial; quantitative colony count, urine |

Arrows point to columns labeled 504, 504, 504, 506.

FIGURE 5A

MBA Final Report

| Billed Rev Code | Billed Units | Bill Type | Bill Date | Billed CPT | LMRP Code | LMRP | NCD Code | NCD | CCI Code | CCI | Verip | Fee Sched Amount | Net Paid |
|---|---|---|---|---|---|---|---|---|---|---|---|---|---|
| 300 | 1 | 13 | 01/03/2003 through 01/03/2003 | 80048 | None None | | 5990 7881 | (C) (C) | 80448, 81001, 80048, 85025, 80048, 87086 | (C) | | ATP08 | |
| 300 | 1 | 13 | 01/03/2003 through 01/03/2003 | 81001 | 1567 1567 | (C) (C) | 5990 7881 | | 81001, 80048, 81001, 85025, 81001, 87086 | (C) | | 4.43 | |
| 300 | 1 | 13 | 01/03/2003 through 01/03/2003 | 85025 | None None | | 5990 7881 | (C) (C) | 85025, 80048, 85025, 81001, 85025, 87086 | (C) | | 10.86 | |
| 300 | 1 | 13 | 01/03/2003 through 01/03/2003 | 87086 | | | 5990 7881 | (C) (C) | 87086, 80048, 87086, 81001, 87086, 85025 | (C) (C) | G00f Charge Not Found | 11.25 11.83 Tot 38.40 | 37.97 |

| ICDS CODE | TEST NAME | TEST CODE | ICDS CODE | TEST NAME | TEST CODE | ICDS CODE | TEST NAME | TEST CODE |
|---|---|---|---|---|---|---|---|---|
| | GENERAL LAB TESTING | | | | | | | |
| | ☐ Alumin | (ALB) | | ☐ HDL Cholesterol | (HDLB) | | ☐ Thyroid Harmone Uptake | (T3U) |
| | ☐ Alpha Fetoprotein (Tumor) | (AFPT) | | ☐ H | (HPELIS) | | ☐ Thyroid Harmone | (TBH) |
| | ☐ Alkaline Phosphatase | (ALKP) | | ☐ Hemoglobin AtC | (HGBA1C) | | ☐ Thyroid Total | (T4) |
| | ☐ ALT (GPT) | (ALT) | | ☐ HepC Load (Quart) | (HEPCVL) | | ☐ Tissue Transglutaminese IgG | (TTGG) |
| | ☐ ANA* | (ANAHU) | | ☐ Hepatitis B Surface Antigen* | (HBSAG) | | ☐ Tissue IgA | (TTGG) |
| | ☐ AST (GOT) | (AST) | | ☐ Hepatitis B One Antibody | (HBCAB) | | ☐ Total Protein | (TP) |
| | ☐ Bilirubin Total | (TBIL) | | ☐ Hepatitis B Surface Antibody | (HBSAB) | | ☐ Triglyceride | (TRIGB) |
| | ☐ BNP | (BNP) | | ☐ Hepatitis C Antibody | (HCVAB) | | ☐ Troponin 1 | (TROP1) |
| | ☐ B/T Cell Subnets (Flow) | (CDO) | | ☐ Hepatitis A Antibody IgM | (HAVM) | | ☐ Troponin w/reflex MB | (TNMB) |
| | ☐ BUN | (BUN) | | ☐ High Electronph | (HGBEP) | | ☐ Uric Acid | (URIC) |
| | ☐ Calcium | (CA) | | ☐ HIV Antibody | (HIV12) | | ☐ Valproate | (VALP) |

FIGURE 7A

| Patient Name | Encounter Number | Physician | Status | Medical Record# | Order | Test Code | Phy Dx 1 | Phy Dx 2 | Phy Dx 3 | Phy Dx4 | Order Date |
|---|---|---|---|---|---|---|---|---|---|---|---|
| Jones Joe | 3065128401 | Abel | OP | 39xxx | Comprehensive Chem Panel | CPCOM | 782.1 | | | | 20040310 |
| Jones Joe | 3065128401 | Abel | OP | 39xxx | TSH w/Reflex Free T4 | TSHR | 782.1 | | | | 20040310 |
| Jones Joe | 3064979309 | Abel | OP | 39xxx | Comprehensive Chem Panel | CPCOM | 282.2 | | | | 20040304 |
| Jones Joe | 3064979309 | Abel | OP | 39xxx | Hemoglobin A1C | HGBA1C | 250.9 | | | | 20040304 |
| Jones Joe | 3065091609 | Abel | OP | 39xxx | Lipid Panel | LIPID | 272.2 | | | | 20040309 |
| Jones Joe | 3065091609 | Abel | OP | 39xxx | Lipid Panel | LIPID | 272.0 | | | | 20040309 |
| Jones Joe | 3065091609 | Abel | OP | 39xxx | HCRP | HCRP | 401.1 | | | | 20040309 |
| Smith, Dorothy | 3064119427 | Ryan | OP | 41xxxx | CBC w/Platelets | CBC | 722.0 | | | | 20040302 |
| Smith, Dorothy | 3064119427 | Ryan | OP | 41xxxx | Basic Chem Panel | CPBAS | 722.0 | | | | 20040302 |
| Smith, Dorothy | 3064119427 | Ryan | OP | 41xxxx | Phosphorous | PHOS | 722.0 | | | | 20040302 |
| Smith, Dorothy | 3064119427 | Ryan | OP | 41xxxx | Magnesium | MG | 722.0 | | | | 20040302 |
| Smith, Dorothy | 3064119427 | Ryan | OP | 41xxxx | Partial Thromboplastin | PTT | 722.0 | | | | 20040302 |
| Smith, Dorothy | 3064119427 | Ryan | OP | 41xxxx | Prothrombin Time | PT | 722.0 | | | | 20040302 |
| Smith, Dorothy | 3064119427 | Ryan | OP | 41xxxx | Type and Screen | TAS | 722.0 | | | | 20040302 |
| Smith, Dorothy | 3064119427 | Ryan | OP | 41xxxx | Urinalysis | UASCR | 722.0 | | | | 20040302 |
| Black Norman | 3064870987 | Hughes | OP | 55xxxx | CBC w/Platelets | CBC | 285.9 | | | | 20040301 |
| Black Norman | 3064870987 | Hughes | OP | 55xxxx | Basic Chem Panel | CPBAS | 585 | | | | 20040301 |
| Black Norman | 3064870987 | Hughes | OP | 55xxxx | TSH w/Reflex Free T4 | TSHR | 311 | | | | 20040301 |
| Coleman Mike | 3064902483 | Smith | OP | 66xxxx | Comprehensive Chem Panel | CPCOM | 729.1 | | | | 20040303 |
| Coleman Mike | 3065156931 | Smith | OP | 66xxxx | Comprehensive Chem Panel | CPCOM | 272.4 | 401.4 | | | 20040311 |
| Coleman Mike | 3065156931 | Smith | OP | 66xxxx | Albumin/Creatinine Ratio | UACR | 401.4 | | | | 20040311 |
| Coleman Mike | 3065156931 | Smith | OP | 66xxxx | Urinalysis | UASCR | 401.4 | | | | 20040311 |
| Coleman Mike | 3065156931 | Smith | OP | 66xxxx | VAP | QVAP | 272.4 | | | | 20040311 |
| Brown, Estelle | 3065037784 | Peters | OP | 77xxxx | CBC w/Platelets | CBC | 414.0 | | | | 20040308 |
| Brown, Estelle | 3065037784 | Peters | OP | 77xxxx | CBC w/Platelets | CBC | 414.0 | | | | 20040308 |
| Brown, Estelle | 3065037784 | Peters | OP | 77xxxx | CBC w/Platelets | CBC | 414.0 | | | | 20040308 |
| Thomposon, Donna | 3065202578 | Westin | OP | 88xxxx | Comprehensive Chem Panel | CPCOM | 250.00 | | | | 20040312 |
| Thomposon, Donna | 3065202578 | Westin | OP | 88xxxx | CK | CPK | 272.0 | | | | 20040312 |
| Thomposon, Donna | 3065202578 | Westin | OP | 88xxxx | Lipid Panel | LIPID | 272.0 | | | | 20040312 |
| Thomposon, Donna | 3065202578 | Westin | OP | 88xxxx | Hemoglobin A1C | HGBA1C | 250.0 | | | | 20040312 |

| Patient Name | PNC | Service From | Thru | MRN | BillType | HCPC Amt | Net Reimb AMT | Remark CDS |
|---|---|---|---|---|---|---|---|---|
| Jones Joe | 3.065E+09 | 20040305 | 20040305 | 1776003 | 130 | 226 | 0 | |
| Smith, Dorothyy | 3.064E+09 | 20040301 | 20040301 | 1242607 | 131 | 173 | 87.25 | |
| Black Norman | 3.065E+09 | 20040302 | 20040302 | 1772958 | 131 | 104 | 74.79 | |
| Coleman Mike | 3.065E+09 | 20040303 | 20040303 | 92044 | 131 | 22 | 5.49 | |
| Coleman Mike | 3.065E+09 | 20040303 | 20040303 | 1759052 | 131 | 420 | 191.7 | |
| Brown, Estelle | 3.065E+09 | 20040304 | 20040304 | 1324606 | 131 | 133 | 49.1 | |
| Thomposon, Donna | 3.065E+09 | 20040308 | 20040308 | 1087614 | 131 | 169 | 98.26 | |

| MRN | PT NAME | ACCNT | COLL DATE | ORDER CODE | ORDER NAME | TEST NAME | RESULTS |
|---|---|---|---|---|---|---|---|
| 39xxx | Jones Joe | 3064979309 | 03/02/2004 | QOP | O AND P CONC AN | PRESERVATIVE | PVA FORMALIN |
| 39xxx | Jones Joe | 3064979309 | 03/02/2004 | QOP | O AND P CONC AN | O AND P CONCENT | NO OVA OR PARASITES |
| 39xxx | Jones Joe | 3055091609 | 03/02/2004 | QOP | O AND P CONC AN | O AND P TRICHRO | NO OVA OR PARASITES |
| 39xxx | Jones Joe | 3055091609 | 03/02/2004 | CAMCHG | CAMPYLOBACTER E | CAMPYLOBACTER E | BILLED FOR SERVICES |
| 41xxx | Smith, Dorothy | 3064119427 | 03/02/2004 | FL | FECAL LEUKOCYTE | FECAL LEUKOCYTE | NO FECAL LEUKOCYTES |
| 41xxx | Smith, Dorothy | 3064119427 | 03/02/2004 | FL | FECAL LEUKOCYTE | REPORT STATUS | FINAL 03032004 |
| 41xxx | Smith, Dorothy | 3064119427 | 03/02/2004 | FL | FECAL LEUKOCYTE | SPECIMEN DESCRI | STOOL |
| 41xxx | Smith, Dorothy | 3064119427 | 03/02/2004 | FL | FECAL LEUKOCYTE | SPECIAL REQUEST | NONE |
| 41xxx | Smith, Dorothy | 3064119427 | 03/02/2004 | STC | CULTURE, STOOL | RESULTS | NO SALMONELLA OR SH |
| 41xxx | Smith, Dorothy | 3064119427 | 03/02/2004 | STC | CULTURE, STOOL | REPORT STATUS | FINAL 03072004 |
| 41xxx | Smith, Dorothy | 3064119427 | 03/02/2004 | STC | CULTURE, STOOL | SPECIMEN DESCRI | STOOL |
| 41xxx | Smith, Dorothy | 3064119427 | 03/02/2004 | STC | CULTURE, STOOL | SPECIAL REQUEST | NONE |
| 41xxx | Smith, Dorothy | 3064119427 | 03/02/2004 | XADD1 | CULTURE ORGANIS | CULTURE ORGANIS | BILLED FOR SERVICES |
| 55xxx | Black Norman | 3064870987 | 03/02/2004 | PSA | PROSTATE SPECIF | PROSTATE SPECIF | 1.86 |
| 55xxx | Black Norman | 3064870987 | 03/12/2004 | UADPOC | URINALYSIS DIPS | URINE CLARITY | HAZY* |
| 55xxx | Black Norman | 3064870987 | 03/12/2004 | UADPOC | URINALYSIS DIPS | URINE COLOR | YELLOW |
| 66xxx | Coleman Mike | 3064902483 | 03/12/2004 | UADPOC | URINALYSIS DIPS | OPERATOR ID | BRF |
| 66xxx | Coleman Mike | 3065156931 | 03/12/2004 | UADPOC | URINALYSIS DIPS | SPECIFIC GRAVIT | 1.01 |
| 66xxx | Coleman Mike | 3065156931 | 03/12/2004 | UADPOC | URINALYSIS DIPS | SOURCE | RANDOM |
| 66xxx | Coleman Mike | 3065156931 | 03/12/2004 | UADPOC | URINALYSIS DIPS | URINE UROBILINO | NORMAL |
| 77xxx | Brown, Estelle | 3065037784 | 03/12/2004 | UADPOC | URINALYSIS DIPS | URINE BILIRUBIN | NEGATIVE |
| 77xxx | Brown, Estelle | 3065037784 | 03/12/2004 | UADPOC | URINALYSIS DIPS | URINE BLOOD | NEGATIVE |
| 77xxx | Brown, Estelle | 3065037784 | 03/12/2004 | UADPOC | URINALYSIS DIPS | URINE COMMENT | <<DO NOT REPORT>> |
| 88xxx | Thompson, Donna | 3065202578 | 03/12/2004 | UADPOC | URINALYSIS DIPS | URINE GLUCOSE | NEGATIVE |

| DEPT | SUBDEPT | CDM # | DESCRIPTION | R/C | CPT | STATUS |
|---|---|---|---|---|---|---|
| LAB | BLOOD | 40221000 | TRANSFUSE FFP | 390 | P9017 | A |
| LAB | BLOOD | 40221003 | ANTIBODY ID | 390 | 86870 | A |
| LAB | BLOOD | 40221004 | COOMBS, DIRECT | 390 | 86880 | A |
| LAB | BLOOD | 40221005 | COOMBS, INDIRECT | 300 | 86885 | A |
| LAB | BLOOD | 40221006 | DU BLOOD TYPE | 300 | 86905 | A |
| LAB | BLOOD | 40221007 | THAW FFP | 390 | 86927 | A |
| LAB | BLOOD | 40221008 | TRANSFUSE GRANULOCYTES | 390 | P9050 | A |
| LAB | BLOOD | 40221009 | GROUP ABO TYPING | 300 | 86900 | A |
| LAB | BLOOD | 40221010 | RH TITER | 302 | 86886 | I |
| LAB | BLOOD | 40221011 | RHOGAM VIAL | 636 | J2790 | A |
| LAB | BLOOD | 40221012 | TRANSFUSE PRC | 390 | P9021 | A |
| LAB | BLOOD | 40221013 | TRANSFUSE WASHED PC | 390 | P9022 | A |
| LAB | BLOOD | 40221014 | XMATCH AND TRANS & WASH | 391 |  | I |
| LAB | BLOOD | 40221015 | TRANS WB | 390 | P9010 | A |
| LAB | BLOOD | 40221016 | XMATCH IMMEDIATE SPIN | 300 | 86920 | A |
| LAB | BLOOD | 40221017 | PLATELETS | 390 | P9019 | A |
| LAB | BLOOD | 40221019 | RH BLOOD TYPING | 300 | 86901 | A |
| LAB | BLOOD | 40221020 | ANTIGEN SCREEN EA (UNIT TEST) | 300 | 86903 | A |
| LAB | BLOOD | 40221023 | TYPE AND SCREEN EA, SERUM | 302 | 86850 | I |
| LAB | BLOOD | 40221024 | TRANSFUSE CRYOPRECIP. | 390 | P9012 | A |
| LAB | BLOOD | 40221028 | COLD ABSORPTION | 390 | 86978 | A |
| LAB | BLOOD | 40221029 | TRANSFUSION REACTION EVAL | 305 | 86078 | A |
| LAB | BLOOD | 40221031 | HIV | 302 | 86701 | A |
| LAB | BLOOD | 40221032 | WESTERN BLOT CONFIRMATION HIV | 302 | 86689 | A |
| LAB | BLOOD | 40221033 | HIV-1 PCR | 306 | 87535 | A |
| LAB | BLOOD | 40221034 | HIV-1 RNA BDNA VIRAL LOAD | 306 | 87536 | A |
| LAB | BLOOD | 40221035 | SYPHILIS, QUAL | 302 | 86592 | I |
| LAB | BLOOD | 40221036 | SYPHILIS, QUANT | 302 | 86593 | I |
| LAB | BLOOD | 40221037 | RHEUMATOID FACTOR, QUAL | 302 | 86430 | A |
| LAB | BLOOD | 40221043 | TRANSFUSE AUTO PC | 390 | P9021 | A |
| LAB | BLOOD | 40221044 | TRANSFUSE AUTO WB | 390 | P9010 | A |
| LAB | BLOOD | 40221045 | TRANSFUSE WITH PALL FILTER | 390 | P9016 | A |
| LAB | BLOOD | 40221046 | TRANSFUSE LEUK PLAT | 390 | P9031 | A |
| LAB | BLOOD | 40221047 | ANTIGEN TYPING EA (PATIENT TES | 300 | 86905 | A |
| LAB | BLOOD | 40221048 | POOLING PLATELETS, EA UNIT | 390 | 86965 | A |
| LAB | BLOOD | 40221049 | IRRADIATION BLOOD, EA UNIT | 300 | 86945 | A |
| LAB | BLOOD | 40221050 | COLLECTION PROCESSING STAT | 302 | 86890 | I |
| LAB | BLOOD | 40221900 | BLOOD BANK MISCELLANEOUS | 399 |  | I |
| LAB | BLOOD | 40221901 | REF LAB ID | 390 | 86870 | A |
| LAB | BLOOD | 40221902 | DESIGNATED DONATION | 390 |  | A |
| LAB | BLOOD | 40221903 | AUTOLOGUOUS UNIT | 390 |  | A |
| LAB | BLOOD | 40221904 | SINGLE DONOR PLATELET | 390 | P9035 | A |
| LAB | BLOOD | 40223000 | AHG-XM ADDED CHARGE PER UNIT | 390 | 86922 | A |
| LAB | BLOOD | 40223001 | ANTIBODY TITER | 300 | 86886 | A |
| LAB | BLOOD | 40223002 | ANTIGEN NEGATIVE PRBC ARC | 390 | P9021 | A |
| LAB | BLOOD | 40223003 | CMV NEGATIVE PRBC ARC | 390 | P9021 | A |
| LAB | BLOOD | 40223004 | ELUTION STUDIES | 390 | 86860 | A |
| LAB | BLOOD | 40223005 | FRESH UNIT ARC | 390 | P9010 | A |
| LAB | BLOOD | 40223006 | HEMOGLOBIN S NEGATIVE PRBC | 390 |  | I |
| LAB | BLOOD | 40223007 | LEUKOCYTE REMOVAL FILTER | 272 | 99070 | A |
| LAB | BLOOD | 40223008 | MULTIPLE BAG ARC | 272 | 99070 | A |

FIGURE 7E

| Field 3 (encounter#) | Field 4 (Bill type) | Field 6 From | Field 6 Through | Field 12 name | Field 23 Medical Record # | Field 42 Rev CD | Field 43 Description | Field 44 HCPCS/ RATEs | Field 45 Serv Date | Field 46 Serv Units | Field 48 Non-covered Charges | field 50 Payer | Field 67 principal diagnosis | Field 68 code (more diagnosis | Field 69 code (more diagnosis | Field 70 code (more diagnosis |
|---|---|---|---|---|---|---|---|---|---|---|---|---|---|---|---|---|
| 74299602 | 131 | 010303 | 010303 | Appleton, Angela | 431598 | 300 | Laboratory | 80048 | 010303 | 1 | | Medicare | 5990 | 7881 | | |
| | | | | | | 300 | Laboratory | 81001 | 010303 | 1 | | Medicare | 5990 | 7881 | | |
| | | | | | | 300 | Laboratory | 85025 | 010303 | 1 | | Medicare | 5990 | 7881 | | |
| | | | | | | 300 | Laboratory | 87086 | 010303 | 1 | | Medicare | 5990 | 7881 | | |
| 75538921 | 141 | 020903 | 020903 | Buster, bill | 449780 | 300 | Laboratory | G0001 | 020903 | 1 | | Medicare | 5939 | 2724 | | |
| | | | | | | 300 | Laboratory | 80048 | 020903 | 1 | | Medicare | 5939 | 2724 | | |
| | | | | | | 300 | Laboratory | 80061 | 020903 | 1 | | Medicare | 5939 | 2724 | | |
| | | | | | | 300 | Laboratory | 80076 | 020903 | 1 | | Medicare | 5939 | 2724 | | |
| 77732145 | 141 | 030403 | 030403 | Charles, Chuck | 467293 | 300 | Laboratory | 85610 | 030403 | 1 | | Medicare | V5861 | | | |
| 71638470 | 141 | 012603 | 012603 | Dolittle, Diane | 492037 | 300 | Laboratory | 86304 | 012603 | 1 | | Medicare | 1830 | | | |
| 75532011 | 141 | 033003 | 033003 | Eaton, Edgar | 428109 | 300 | Laboratory | G0001 | 033003 | 1 | | Medicare | 79093 | | | |
| 75540707 | 131 | 090503 | 090503 | Murray, Adam | 412760 | 300 | Laboratory | 80048 | 090503 | 1 | | Medicare | 41400 | 4280 | 4279 | 78841 |
| 75540707 | 131 | 090503 | 090503 | Murray, Adam | 412760 | 301 | Laboratory | 84443 | 090503 | 1 | | Medicare | 41400 | 4280 | 4279 | 78841 |
| 75540707 | 131 | 090503 | 090503 | Murray, Adam | 412760 | 301 | Laboratory | 81001 | 090503 | 1 | | Medicare | 41400 | 4280 | 4279 | 78841 |
| 75540707 | 131 | 090503 | 090503 | Murray, Adam | 412760 | 301 | Laboratory | 87088 | 090503 | 1 | | Medicare | 41400 | 4280 | 4279 | 78841 |
| 75224117 | 141 | 090403 | 090403 | James, Bill | 421892 | 305 | Laboratory | 85610 | 090403 | 1 | | Medicare | V433 | | | |
| 75123628 | 131 | 082203 | 082203 | Christen, Mary | 473457 | 300 | Laboratory | 88142 | 082203 | 1 | | Medicare | V762 | | | |
| 75558230 | 141 | 072903 | 072903 | Stanley, Tim | 586275 | 301 | Laboratory | 84295 | 072903 | 1 | | Medicare | V709 | | | |
| 75404053 | 141 | 090303 | 090309 | Buck, Joan | 217962 | 300 | Laboratory | G0001 | 090309 | 1 | | Medicare | 78900 | | | |
| 75404053 | 141 | 090303 | 090309 | Buck, Joan | 217962 | 301 | Laboratory | 82378 | 090309 | 1 | | Medicare | 78900 | | | |
| 75404053 | 141 | 090303 | 090309 | Buck, Joan | 217962 | 302 | Laboratory | 86301 | 090309 | 1 | | Medicare | 78900 | | | |
| 75004043 | 131 | 080303 | 080303 | Smith, Larry | 473210 | 301 | Laboratory | 82330 | 080303 | 1 | | Medicare | 2753 | | | |
| 73004776 | 131 | 071203 | 071203 | Jones, Mary | 479321 | 301 | Laboratory | 81001 | 071203 | 1 | | Medicare | 4779 | | | |
| 75814354 | 131 | 042303 | 042303 | Kemp, Alex | 413897 | 300 | Laboratory | 80053 | 042303 | 1 | | Medicare | 5990 | 7881 | | |
| 75814354 | 131 | 042303 | 042303 | Kemp, Alex | 413897 | 301 | Laboratory | 80061 | 042303 | 1 | | Medicare | 5990 | 7881 | | |
| 75814354 | 131 | 042303 | 042303 | Kemp, Alex | 413897 | 300 | Laboratory | G0001 | 042303 | 1 | | Medicare | 5990 | 7881 | | |
| 76143970 | 141 | 062803 | 062803 | Brown, Rosemary | 443724 | 301 | Laboratory | 87535 | 062803 | 1 | | Medicare | 042 | | | |
| 76143970 | 141 | 062803 | 062803 | Brown, Rosemary | 443724 | 301 | Laboratory | 87536 | 062803 | 1 | | Medicare | 042 | | | |
| 76143970 | 141 | 062803 | 062803 | Brown, Rosemary | 467560 | 305 | Laboratory | 85018 | 073103 | 1 | | Medicare | 042 | | | |
| 74961250 | 131 | 073103 | 073103 | Moore, Jessie | 467560 | 305 | Laboratory | 85008 | 073103 | 1 | | Medicare | 78469 | | | |
| 74961250 | 131 | 073103 | 073103 | Moore, Jessie | 478925 | 301 | Laboratory | 83090 | 081303 | 1 | | Medicare | 78469 | | | |
| 73159753 | 131 | 081303 | 081303 | Stocken, Mary | 478925 | 301 | Laboratory | 82127 | 081303 | 1 | | Medicare | 74600 | | | |
| 73159753 | 131 | 081303 | 081303 | Stocken, Mary | 441978 | 300 | Laboratory | G0001 | 071503 | 1 | | Medicare | 74900 | | | |
| 73996411 | 131 | 071503 | 071503 | Black, Philip | 441978 | 305 | Laboratory | 85595 | 071503 | 1 | | Medicare | 2866 | | | |
| 73996411 | 131 | 071503 | 071503 | Black, Philip | | | | | | | | | 2866 | | | |

| SQ | Desc | CDM |
|---|---|---|
| BPFT | Bedside PFT | 31701026 |
| ABG | Arterial Blood Gas | 31701030 |
| ABGCO | ABG/CO-OXIMETER | 31701030 |
| CBG | Capillary Blood Gas | 31701030 |
| ABGCO | ABG/CO-OXIMETER | 31701041 |
| COHB | Carboxyhemaglobin | 31701041 |
| POXY | Pulse Oximetry | 31701050 |
| WS | Weaning Spirometry | 31701052 |
| PH | PH | 31701060 |
| ACHB | Arterial CO Hemaglobin | 31701067 |
| COHB | Carboxyhemaglobin | 31701067 |
| ACHB | Arterial CO Hemaglobin | 31701068 |
| COHB | Carboxyhemaglobin | 31701068 |
| ACHB | Arterial CO Hemaglobin | 31701069 |
| ACHB | Arterial CO Hemaglobin | 31701070 |
| ABG | Arterial Blood Gas | 31701082 |
| ABGCO | ABG/CO-OXIMETER | 31701082 |
| CBG | Capillary Blood Gas | 31701082 |
| COHB | Carboxyhemaglobin | 31701082 |
| BPFT | Bedside PFT | 31711002 |
| ABG | Arterial Blood Gas | 32500004 |
| ABGCO | ABG/CO-OXIMETER | 32500004 |
| CBG | Capillary Blood Gas | 32500004 |
| ANAS | ANA Screen | 40001001 |
| B12 | Vitamin B12 | 40001002 |
| BCABM | Hepatitis B Core IgM | 40001003 |
| CEAFB | CEA Fluid | 40001004 |
| CEAS | CEA Serum | 40001004 |
| FER | Ferritin | 40001008 |
| HBSAG | Hepatitis B Surface Ag. | 40001010 |
| PEL | Protein Electro. | 40001016 |
| PELP | Protein Electrophoresis Urine(Random) | 40001016 |
| PELP24 | Protein Electro, 24hr Urine | 40001016 |
| KTU | THYROID UPTAKE | 40001017 |
| TU | T3 Uptake | 40001017 |
| THYP | Thyroid Profile | 40001020 |
| KTSH | TSH | 40001021 |
| TSH | TSH | 40001021 |
| EBVG | EBV/Epstein Barr Virus Capsid Ab | 40001022 |
| HAPT | Haptoglobin | 40001027 |
| IMFI | Immunofixation Interpretation and Quanti+ | 40001029 |
| IMFI | Immunofixation Interpretation and Quanti+ | 40001029 |
| IMFI | Immunofixation Interpretation and Quanti+ | 40001029 |
| PABL | Phospholipid,Serum | 40001035 |
| FSH24 | FSH, 24 hr Urine | 40001036 |
| KT3 | T3 | 40001037 |
| TT3 | Total T3 | 40001037 |
| FT4 | Free T4 | 40001038 |
| KFT4 | FREE T4 | 40001038 |
| FAVII | Factor VII, Functional | 40001040 |

FIGURE 7G

METHOD, SYSTEM, AND SOFTWARE FOR ANALYSIS OF A BILLING PROCESS

CROSS REFERENCE TO RELATED APPLICATION

This application claims priority to U.S. Provisional Application Ser. No. 60/529,732 filed on Dec. 17, 2003, the disclosure of which is incorporated herein in its entirety.

BACKGROUND OF THE INVENTION

The present invention relates generally to an approach for improved analysis of complex billing processes. For example, the billing and reimbursement process associated with the Medicare or other large government programs is very complex in which a number of parties interact in the entire process of generating the billing information and receiving and tracking the payment corresponding to the billing information. Furthermore, it is also very difficult to audit and track the billing information and the payment received to the underlying services for which the billing and payment is performed. For example, in the context of Medicare, this process involves the provision of medical and laboratory test services to a patient and the reimbursement of the costs thereof from a paying party, such as the authorities that manage the Medicare program.

In this complex process, any errors in the billing process (by a provider of services) may result in the denial of payment by the paying authority. Furthermore, other errors in the billing process by the provider of services may result in an audit by an audit entity or result in fines to the provider simply because the billing process was not managed correctly. Therefore, there is a need for a more efficient process for managing and analyzing the billing process in a complex billing and payment process such as that used in the Medicare billing and payment process.

Furthermore, the provider laboratories are not only responsible for controlling how the services are billed but they are often also responsible for keeping documentation about their compliance with applicable government and other regulations. For example, for Medicare billing and payment, the Office of the Inspector General (OIG) has compliance guidelines which provider laboratories are expected to adhere to.

SUMMARY OF THE INVENTION

In certain embodiments, the present invention provides a computer implemented method of analyzing third party payments for provider services, including the steps of: processing third party payment information data; processing provider services billing data provided to the third party to request payment; automatically validating, on a computing system, provider services billing data against other provider services data including verifying that all billed services indicated in the billing data match actual services performed indicated in the other provider services data; and generating a report listing discrepancies between the third party payment information data, the provider services billing data, and the other provider services data.

In certain embodiments, the step of automatically validating further includes validating the provider services billing data against external data related to the provider services.

In certain embodiments, the step of automatically validating includes validating, for a particular patient encounter, a date of service between the third party payment information data, the provider services billing data, and the other provider services data.

In certain embodiments, the third party payment information data includes Medicare payment information data and the other provider services data includes laboratory services data.

In certain embodiments, the step of automatically validating provider services billing data against external data further includes, for a patient encounter, validating existence of a doctor's order for each service billed in the billing data and validating a test description in the doctor's order for each laboratory service indicated in the laboratory services.

In certain embodiments, the step of automatically validating includes accessing third party provided data to validate particular tests indicated in the laboratory services data with other tests indicated in the laboratory services data.

In certain embodiments, the step of automatically validating includes validating provider services billing data against billing rates for the provider services specified by the third party provided data for the provider services.

In certain embodiments, the step of automatically validating includes validating provider services billing data for a group of billed services to detect duplicate billing of component services that are included in the billing data for the group of billed services.

In certain embodiments, the step of processing the third party payment information data and the step of processing provider services billing data each includes randomly selecting corresponding records including the same one or more patient encounter data.

In certain embodiments, the step of generating a report listing discrepancies includes tracking and classifying discrepancies across multiple reports.

In certain embodiments, the step of generating a report listing discrepancies comprises generating an alert when discrepancies across multiple reports cross a certain threshold.

In certain other embodiments, the present invention provides a system for analyzing third party payments for provider services, including: an input unit that processes third party payment information data and provider services billing data provided to the third party to request payment; a validation unit, connected to the input unit, that validates the provider services billing data against the third party payment information data and other provider services data including verifying that all billed services indicated in the billing data match actual services performed indicated in the other provider services data; and a report unit that generates a report listing discrepancies between the third party payment information data, the provider services billing data, and the other provider services data.

In certain other embodiments, the present invention provides a computer implemented medium having program code recorder thereon that, when executed on a computing system, analyzes third party payments for provider services, the program code including: code for processing third party payment information data; code for processing provider services billing data provided to the third party to request payment; code for automatically validating, on a computing system, provider services billing data against other provider services data including verifying that all billed services indicated in the billing data match actual services performed indicated in the other provider services data; and code for generating a report listing discrepancies between the third party payment information data, the provider services billing data, and the other provider services data.

BRIEF DESCRIPTION OF THE DRAWINGS

FIGS. 5A and 5B are sample reports generated by the billing process analysis in certain embodiments of the present invention.

FIGS. 7A-7G are exemplary files used in certain embodiments of the present invention.

DETAILED DESCRIPTION OF THE VARIOUS EMBODIMENTS

Figure 1:
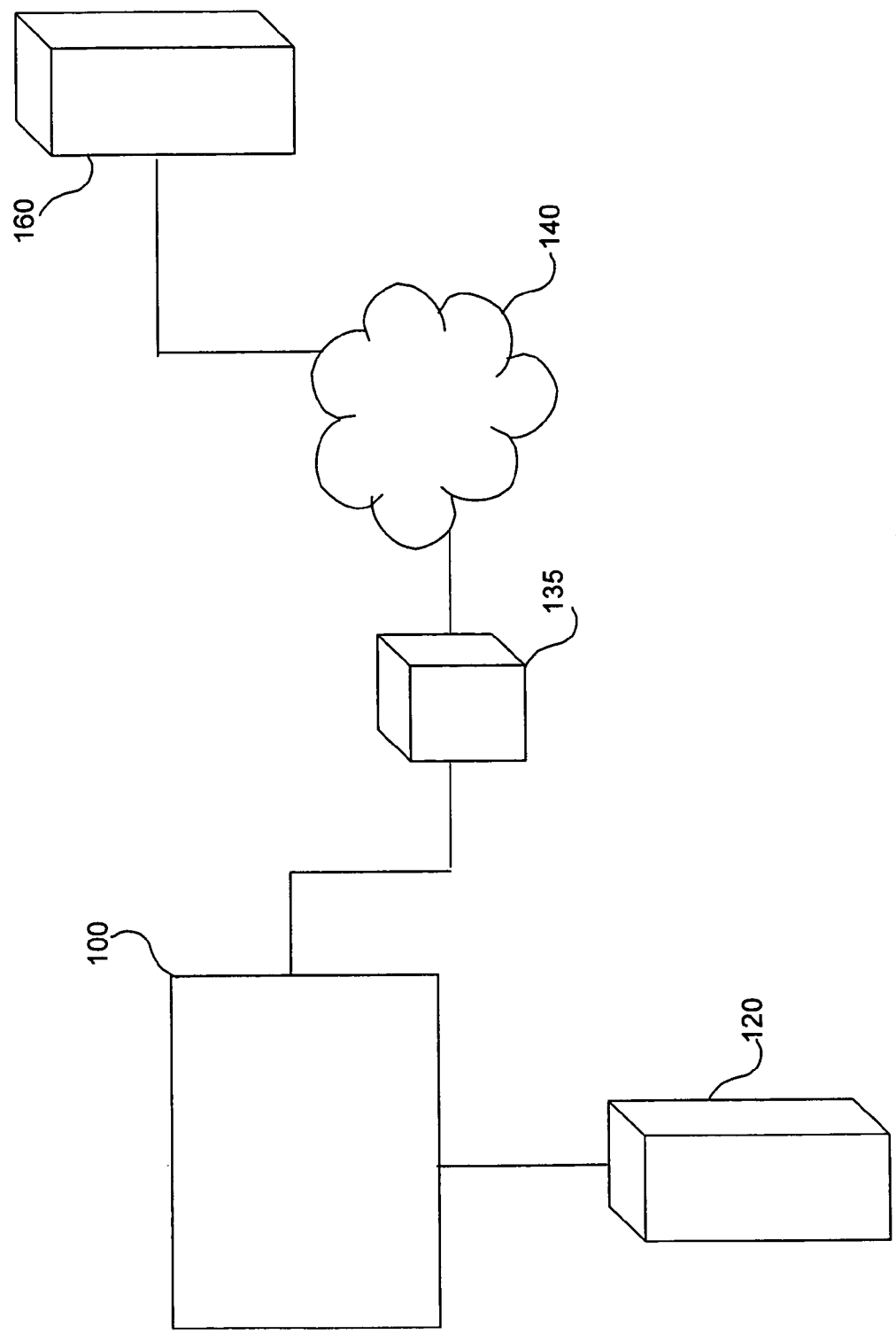
FIG. 1 is a block diagram illustrating the system components in one embodiment of the present invention.

In certain embodiments, the present invention relates to managing the billing and payment receipt for a provider of services to a large government program (as an example of third party providing payments), such as Medicare. Such a provider of services may be a laboratory that provides laboratory services to a patient based on a doctor's or hospital order and then bills the third party program for payment for the services rendered. Typically, the program periodically renders payment to the provider and provides payment information which allows the payments to billing data associated with one or more patient encounters. In certain embodiments, the present invention provides a method, system, and software that analyzes the billing information provided by the provider of services, the payment information provided by the third party providing the payment, the service rendered information provided by the provider of services, and external information related to the services and payments typically provided by, or on behalf, of the third party that provides the payment. This analysis provides a report or other output that automatically identifies any discrepancies between these data sources with respect to the services rendered, the services billed, and the payment received.

In a general aspect, some of the features of the billing process analysis provided by the present invention includes: (1) monitor laboratory claims for payments; (2) keep laboratory management informed on how services and billed and paid; (3) document results of claims; and (4) provide tangible evidence of the compliance effort.

In certain embodiments, the billing process analysis serves as a management tool that provides random sampling by (1) Current Procedural Terminology (CPT) code, (2) International Classification of Diseases (ICD-9) code, and (3) Physician identification code.

In certain embodiments, the billing process analysis analyzes (1) physician orders and requisitions, (2) test results, (3) claims forms (for example, UB-92 and 1500 forms for Medicare claims), and (4) remittance advice from the payment authority (for example, the explanation of Medicare or Medicaid (EOMB) file for Medicare payments).

In certain embodiments, the billing process analysis software validates claim data (or more generically billing data) against (1) internal files including modified Charge Description Master (CDM) file (which contains charge descriptions) and laboratory test directory (which lists laboratory test descriptions); and (2) external files including coding tables, regulatory tables, and fee schedules. That is, the management billing analysis process considers all laboratory test related claim (or billing data) elements that influence the payment from a payment authority such as Medicare.

In certain embodiments, the management billing analysis process provides a detail report that is an accurate representation of how laboratory services are billed by identifying: (1) electronic system issues, (2) procedural issues, (3) compliance related issues, and (4) documentation issues.

In certain embodiments, the primary elements validated include: (1) the physicians order, (2) laboratory test, (3) billed ICD-9 code, (4) date of service, and (5) the CPT and/or healthcare common procedure coding system (HCPCS) codes.

FIG. 1 is a diagram that illustrates a general system in which one embodiment of the management billing analysis software process is provided. It should be understood that FIG. 1 is exemplary only. One skilled in the art would recognize various other modifications and alternatives all of which are considered a part of the present invention. A laboratory computing system 100 contains the management billing analysis software and is connected to a database on a computing system 120 which contains the hospital, laboratory, patient, and billing data. It should be noted that while one database on one computing system 120 is shown to contain this data, one skilled in the art would recognize that the computing system 120 could be distributed computing system and the data could be stored in distributed data stores so long as the management billing analysis software could access the required data in the distributed data stores and/or distributed computing system. The laboratory computing system 100 is also connected through the Internet (or other similar public or private network through a firewall 135, for example) to a reference data store 160. While this reference datastore 160 is shown as being external to the firewall 135, one skilled in the art would recognize that a copy of the external datastore may also be located inside the firewall, for example, and updated by a periodic download or transfer of information from an external location.

Figure 2:
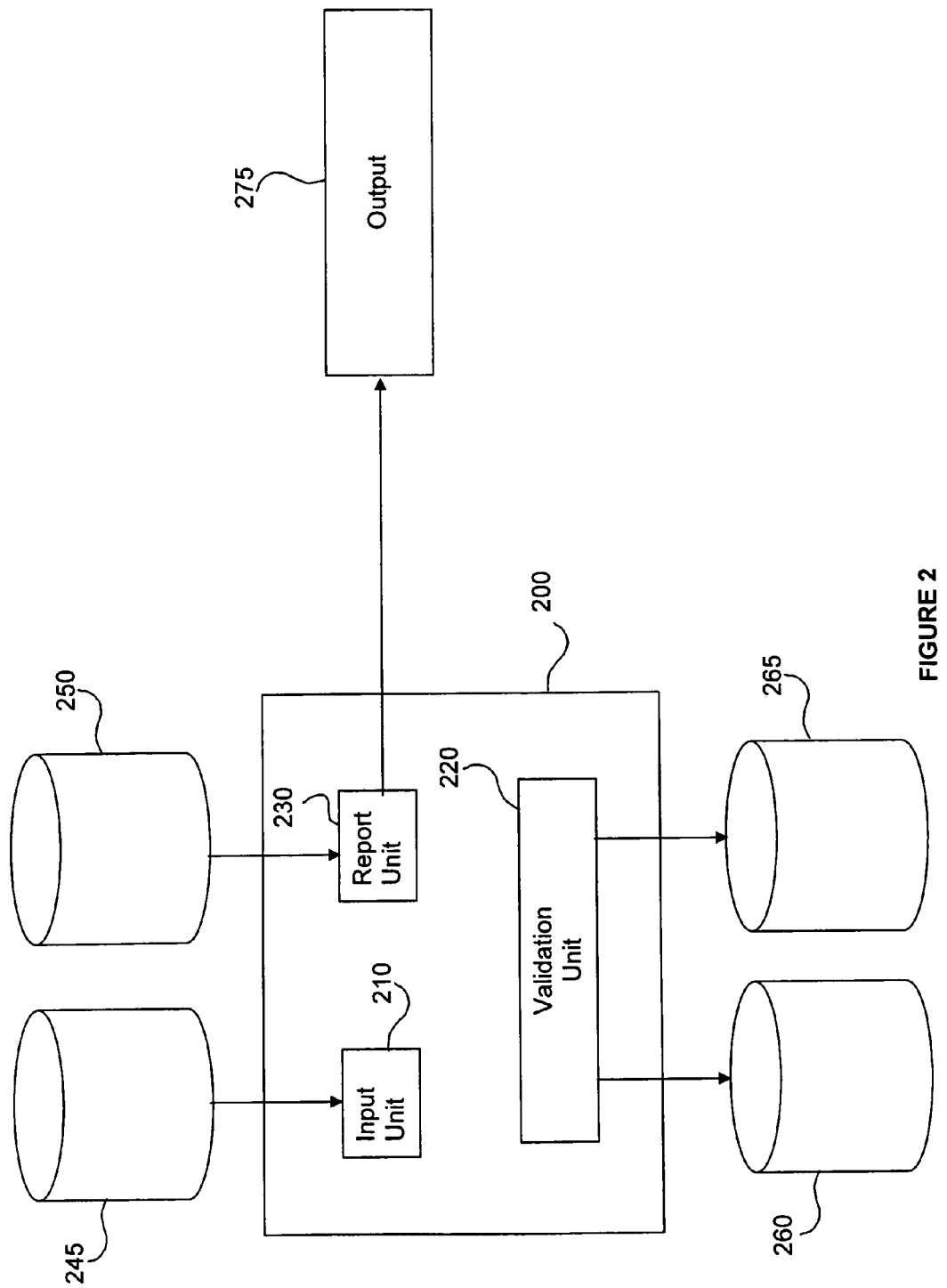
FIG. 2 is a block diagram illustrating the application architecture in certain embodiments of the present invention.

FIG. 2 is a block diagram illustrating the application architecture in certain embodiments of the present invention. It should be understood that FIG. 2 is exemplary only. One skilled in the art would recognize various other modifications and alternatives all of which are considered a part of the present invention. The billing analysis software 200 includes an input unit 210 that accesses both the billing data 245 provided by a provider of services and payment data 250 typically provided by the third party (for example, Medicare) that makes the payment for the services provided by the provider. One skilled in the art would recognize that these data are shown in two separate databases since the source of the data is from different sources. However, in practice, all of this data could be stored in one logical database without altering the principles of the present invention. For example, the provider of services which generates the billing data 245 may also periodically receive the payment data from the third party providing the payment and may store both of these data in one logical database.

A validation unit 220 accesses the billing data and the payment data processed (or simply retrieved) by the input unit 210 and performs various validation checks on this data. The validation checks performed are described in greater detail further herein. In order to perform the validation checks, the validation unit 220 also accesses additional data in databases 260 and 265. For example, the database 260 may contain all the information related to the services rendered by the provider. Therefore, database 260 may contain hospital records, patient records, laboratory records, and doctor records so that all the underlying data used in generating the billing data may be accessed from the database 260. The database 265 represents external data that is used in generating the billing data based on requirements and/or fee schedules that may be specified by the third party payment provider. For example, the third party payments provider may specify the exact fees to be paid for particular services on a state-by-state basis. Likewise, the database 265 may contain data which specifies which services are not covered as well as information on valid or impermissible groupings of services. Therefore, the third party payment provider (for example, Medicare) may specify that certain groups of services must be billed together using a group code or that certain tests are mutually exclusive so that if one is billed than the other must not be billed.

The billing management software provided by certain embodiments of the present invention verify that fees billed match the applicable fee schedules and also that the groups of services billed are consistent with the requirements of the third party payment provider. Therefore, the software verifies that all the grouped services are billed using a group code when a group of services is rendered. The software also verifies that mutually exclusive services are both not billed. The software may use data structures (such as tables) to implement these validation checks. For example, for grouped services, the software may check a table that includes all the services included in a group so that it can check the billing data to verify that the individual services that comprise a group are not separately billed when the group code for the group of services has been billed. Furthermore, the software may verify if the complete set of all tests in a group have been individually billed and if so, it may indicate that the complete set of all test in a group that have been individually billed should be replaced by a single code that represents billing for the group using the group code. It should be recognized that most of these validations are typically performed on a patient/encounter basis. However, in certain embodiments, the software may verify the billing data across multiple patient encounters. For example, if a CBC (Complete Blood Count test) has been performed for a patient encounter it may flag or identify a second CBC performed for that patient within a certain time period (for example, within the same month).

The results of the validation are then formatted by a report unit 230 which displays the results using an output unit 275. For example, the results of the validation may be used to generate a report such as the report 500 illustrated in FIG. 5. Of course, the output of the validation unit 220 may also be provided in various other forms. For example, if certain discrepancies are identified, the report unit may generate automatic e-mail or voicemail alerts to key personnel who are charged with tracking the billing and payment process. Even if no discrepancies are discovered, the results of the validation process can be stored or archived so that they provide an audit trail of the integrity of the provider's billing process and serve as evidence of the compliance by the provider to the applicable rules and regulations related to the billing and payment processing by the provider of services (for example, the provider of laboratory services complying with the applicable Medicare related rules and regulations).

Figure 3:
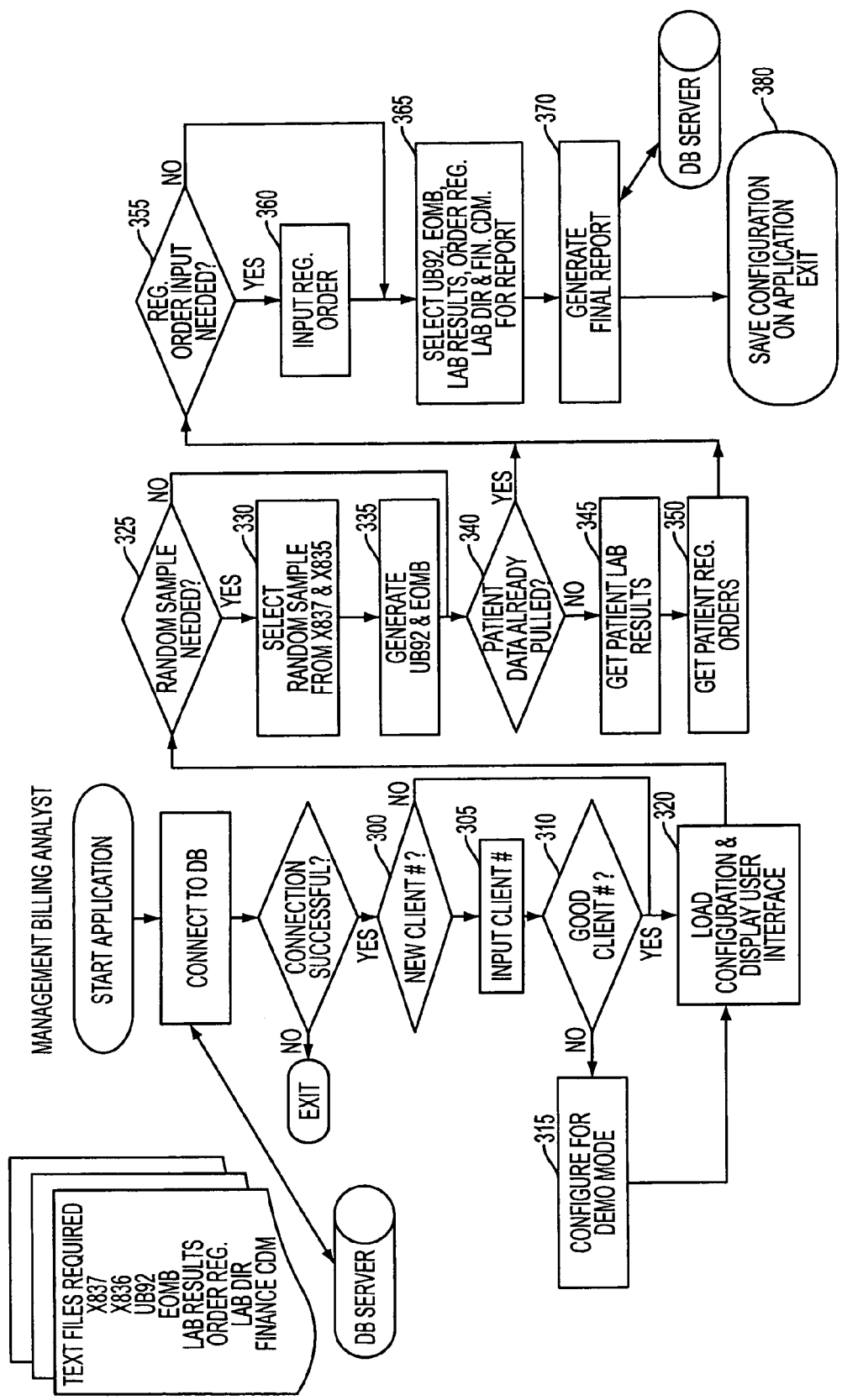
FIG. 3 is a flow diagram illustrating the billing process analysis according to certain embodiments of the present invention.

FIG. 3 is one embodiment of the process flow of the billing analysis software provided by the present invention. In steps 300-320, the software loads the configuration and display for a particular client. For example, each client that uses the software may have a display that includes its own identity. In step 325, the software decides (for example, based on user input or based on the presence or absence of certain data files) whether a random sample is needed (for example, if the data to be analyzed has not yet been selected) and then proceeds to step 330 in which the data for the random sample is selected.

As shown in step 330, the random selection process includes selecting data from electronic files that include provider billing data (X837) and the third party payment data (X835). The selection process of data from these files may be done on any of the data fields of interest for analysis. For example, the selection process may select data based on time period, doctor or physician, particular patients or types of patients (for example, gender and/or age based selection), or based on particular test codes or diagnosis codes. Alternatively, the data selection process may be done on a random basis, for example, for audit purposes. In any selection, all the related records from both the provider billing data file and the third party payment data are selected. For example, for certain selected dates or date range, a unique identifier for a patient (a medical record number) may be used to select all the records from the provider billing data file (X837) and the third party payment data file (X835) that match the selected medical record numbers for the selected certain dates or date range.

In step 335, the selected data is used to generate the billing data file (UB92) and the third party payment data file (EOMB) that is used for the validation process in certain embodiments of the present invention. In step 340, the process checks whether patient data for the selected patient records have been pulled, and if so, proceeds to step 355. If not, the process proceeds to steps 345 and 350 to get the selected patients' laboratory results data from the laboratory datastore and the selected patients' physicians orders (used interchangeably with doctors orders) and order requisition, listing tests ordered, from the laboratory/hospital datastore. In step 355, the process checks whether input of any of the patients' doctors order is required and if so, receives input of the doctors order in step 360.

Thereafter, the process proceeds to step 365 in which the required data files containing the data records for the selected patients are accessed in order to perform the analysis and validation checks provided by certain embodiments of the present invention. In certain embodiments, the files with the relevant records include the following files: (1) UB92 file that contains the provider billing or claim data for the selected patient records; (2) EOMB file that contains payment information from the third party payment provider (for example, Medicare) for the selected patient records; (3) Laboratory Test Results file which contains all laboratory test results for the selected patient records; (4) Order Requisition file which contains all tests ordered by a physician for the selected patient records; (5) laboratory test directory which lists all the tests that can be performed by a laboratory, and (5) finance CDM file which contains a list of descriptions of laboratory tests and various codes that are used for billing the laboratory tests.

The results of the analysis and validation checks are then used to generate a final report in step 370 before the process terminates in step 380.

Some of the validation checks for each patient/encounter that are performed in steps 365 and 370 are described in the following paragraphs with respect to FIG. 4, for example.

(1) Verify that the date for the provider services matches the date on the doctors order and the date on the billed information.

(2) Verify that the laboratory tests ordered by the doctor matches the laboratory tests performed and the laboratory tests billed.

(3) For any group test code billed, verify that each of the component tests (that make up the group) was performed by the laboratory and that none of the component tests were separately billed in addition to the group test code billed. List of group test codes and their respective component tests may be maintained in a data file (such as in a database table). Furthermore, the process may verify that if two or more group tests are ordered which contain a component test in common, the bill is adjusted to ensure that the same component test is not billed twice.

(4) Verify if any mutually exclusive pair of tests performed and/or billed. Pairs of mutually exclusive pairs of tests may be maintained in a data file (such as in a database table).

(5) Verify if any test codes that are not covered were billed. List of not covered test codes may be maintained in a data file (such as in a database file).

(6) Verify if any combinations of test codes/diagnosis codes that are not covered were billed. List of not covered combinations of test codes/diagnosis codes that are not covered may be maintained in a data file (such as in a database file).

(7) Verify if any test or process that should be billed based on the doctor's order is actually included in the billed data even if it is not separately listed on the doctor's order. For example, a doctor may order a blood analysis test which requires a blood collection service that must be separately coded and billed. Therefore, the process checks to verify whether for each blood related test ordered by a doctor, whether the billed data includes a code for the blood collection service.

FIG. 5 is an exemplary analysis report output from the analysis and verification process of one embodiment of the present invention. The report shows at 502 that the whether a laboratory test matched the test ordered by the physician. In columns 504 and 506, the report indicates the patient encounter date and the sample collection date and would indicate a discrepancy if these dates did not match (for example, the sample collection date was earlier than the patient encounter date). The LMRP, NCD, and CCI codes displayed indicate whether particular combinations of tests (whether in a group test code or otherwise) are covered and would indicate a discrepancy if the billed data billed a combination that is not covered.

Figure 4:
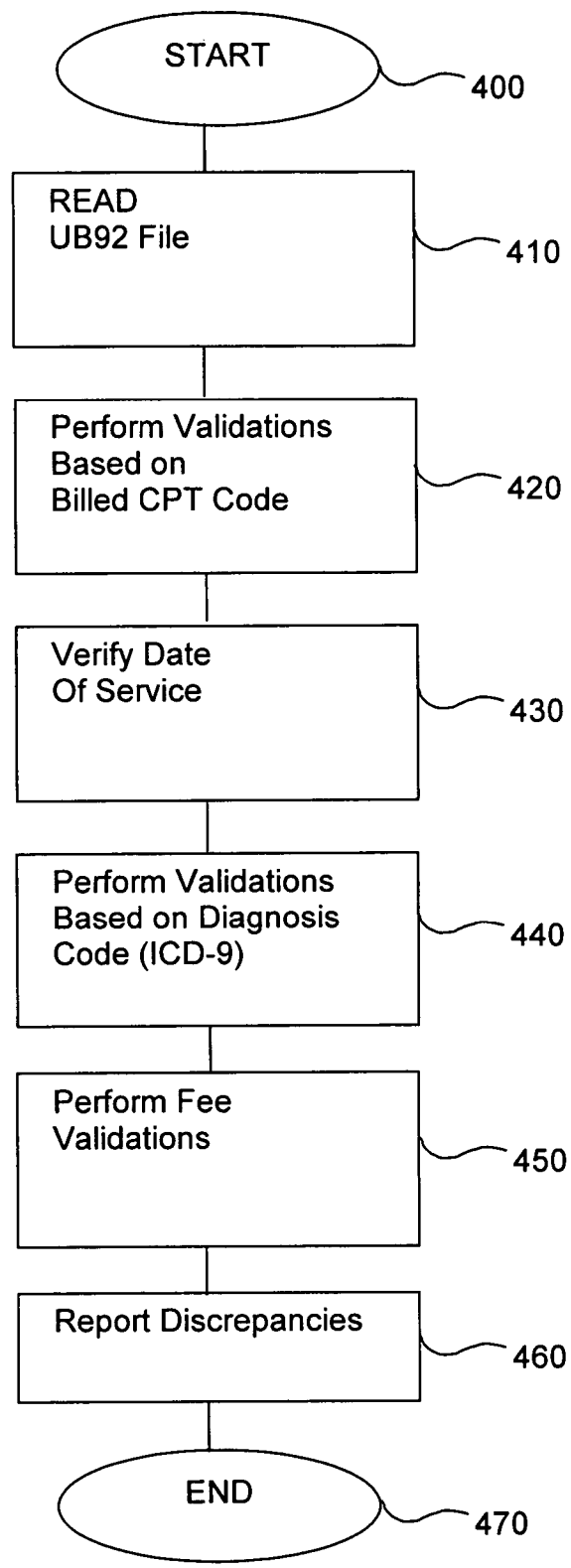
FIG. 4 is a flow diagram illustrating the data analysis that generates the final report in certain embodiments of the present invention.

FIG. 4 is flow chart that discloses one embodiment of the analysis and validity processing performed for billing of laboratory services for payment by Medicare. FIGS. 7A-7F are exemplary formats of the files that are accessed by the analysis and validity processing for the billing of laboratory services for payment by Medicare. This analysis and validity processing may generate the report in the format shown in FIG. 5. It should be recognized that these figures are exemplary only. One skilled in the art would recognize various modifications and alternatives, all of which are considered a part of the present invention.

The process begins in steps 400 and 410 by reading in a file that represents the provider services billing data in a file such as the UB92 file 730 shown in FIG. 7F. The data in the UB92 file, which provides the basis of the services billed, is subject to various validation and checking procedures in the step 420. Typically, the UB92 file contains en entry for each test (or service) billed for each patient/encounter combination. For example, in step 420, the billed CPT/HCPCS code (hereafter "CPT") code may used to perform various validations. The Current Procedural Codes (CPT) codes are provided by the American Medical Association and includes a list of CPT codes with their corresponding descriptions of medical related procedures. The billed CPT code may be verified to check whether it is an active code and if not, it is flagged to be reported as being an inactive code. The CPT code in the UB92 file is used to query a laboratory CDM file (see 725 in FIG. 7E) to pick up a description of the procedure in the laboratories terminology. This description of the procedure (picked up in the laboratory CDM or optionally in a linking laboratory test directory file 735 shown in FIG. 7G) may also be used to verify with the laboratory test results file 720 (in FIG. 7D) to determine that the test procedure was actually performed by the laboratory (for example, based on the description of the test procedure and the dates as discussed in step 430 further herein).

The CPT code may also be used to check other Medicare (as an example of the third party payment provider) files to determine whether the CPT code procedure is covered by Medicare. For example, a NCD, LMRP, and NCCI files may be queried to determine any coverage limitations. As discussed earlier herein, these coverage limitations could include the fact that the CPT code is not covered at all, or not covered with combination with other CPT codes ("mutually exclusive" test) or subject to testing on the basis of whether group coverage applies when this CPT code is also included in a group CPT code. As would be recognized by those skilled in the art, some or all of these verifications may be performed on a state-by-state basis based on access to data for the states (for example, in accessible database tables). Finally, the validation process in step 420 may also check to see if any special procedures should have been coded for certain billed CPT codes. For example, if the billed CPT code relates to a blood related test, a blood collection code should have been inserted and billed to ensure complete reimbursement to the provider of the provider services. Such a verification could be performed based on rules included in the program logic or reference data tables maybe provided which specify any special procedures which should be billed correlated to the other billed procedures related thereto.

In step 430, the process verifies the date of service between the various files to ensure that the billed services correspond to actual services performed. Typically, services are matched based on a combination of a patient's identification number (unique to a patient) and encounter number (unique for each patient) basis. For example, in the UB92 form 730, the patient's identification number is shown in field 23 (Medical Record Number) and encounter number is shown in field 3. The service date is shown in field 45. The service date in the UB92 file is verified against the service and collection date shown in the laboratory test data file 720 shown in FIG. 7D and the order requisition file 710 shown in FIG. 7B (with the match being performed for each patient's identification number and encounter number combination as the key). Therefore, for example, the service date in field 45 of the UB92 file 730 is compared to the collection date in the laboratory test data file 720 and the order date shown in the order requisition file 710. The comparison could validate, for example, that the collection date and the service date are both on or after the order date and the service date is on or after the collection date. In case these comparisons do not validate, a flag can be set to report out a discrepancy in the dates related to a billed service.

In step 430, the patient/encounter identification information and the service dates can also be used to verify that all the billed services (in the UB92 file) were actually performed and if not that fact is flagged for reporting. Furthermore, the process in step 430 may also verify that the billed service and the service ordered and performed actually match the service ordered by the doctor or physician. Therefore, the process may verify that all the billed services are matched by tests ordered on a physicians order, such as the exemplary physician's order 705 shown in FIG. 7A. If any test has been billed for which there is no corresponding test on the physician's order, this fact is flagged and automatically indicated in the report. The match between the billed service and the physician's order may be performed using one or more of the following information: patient's identification information and service date (for example, medical record number and encounter date or patient's name and gender), the test name or description, the diagnosis code (for example, ICD-9 code), date of order or date of service, or doctor name. The automated detection of a mismatch between the billed services and the tests ordered in the physician's order (in particular, tests billed but not supported by a physician's order) is a feature provided by the present invention which may proactively prevent one of the important discrepancies that may be detected by a later external audit since a provider can take corrective action once the discrepancy is detected.

Other matches are also performed in this step. For example, the test code description picked from the laboratory files (either the CDM file 725 or the laboratory test directory file 735) may be matched to one or both of the description in the order requisition file 710 or the description on the physician's order 705 that may be stored in electronic form to facilitate the automated matching to the physician's order provided in certain embodiments of the present invention.

In step 440, the process performs additional validations based on the diagnosis codes (for example, ICD-9 codes) that may also be found on the physician's order. Medicare may provide tables that provide permissible or impermissible combinations of CPT codes with ICD-9 codes. These combinations can be checked to determine whether the billed service is permissible based on all the combinations of the CPT codes billed together with their associated ICD-9 codes. If the billed service is not permissible based on the combination of the billed CPT codes and their associated ICD-9 diagnosis codes provided by the physician, a discrepancy is flagged for reporting.

In step 450, the process reads the file provided by the third party payment provider, for example, the EOMB file 715 provided by Medicare, to determine whether the reimbursed payments from Medicare are correct. In order to determine the correct payment, the process consults external fee schedules provided by Medicare (or other third party payment provider) and calculates the fee that should be received for all valid billed services. If there are any discrepancies in the fee reimbursed by the third party payment provider (e.g., Medicare), that fact is also flagged for reporting purposes.

Finally, in step 460, the process generates a display or report (or other communication) that displays all the transactions from the UB92 file that it checked and reports or highlights any discrepancies identified. Even if no discrepancies are identified, a report may be generated identifying every transaction verified so that the report may be stored or archived for audit or compliance purposes.

Some of the benefits of the management billing process analysis software provided by certain embodiments of the present invention include the fact that it provides a retrospective analysis to determine regulatory compliance and also identify systemic or compliance errors. This is in sharp contrast to other known front-end programs that are prospective in nature and tend to identify factors that may limit payment. The management billing process analysis software provides data and reports that document the compliance efforts. Furthermore, the analysis provided herein can be used by a laboratory to take corrective action to prevent recurrence of problems identified in the analysis process.

It should also be noted that while certain embodiments of the present invention have been discussed with respect to a billing and payment process for laboratory services provided to patients in which reimbursement is provided by a large third party payment authority such as Medicare, the analysis and validation discussed herein may be applied to many other billing and payment processes. In particular, the analysis and validation discussed herein would be applicable to other areas such as cardiology, radiology, physical therapy, etc. where the provider services need to be validated with respect to ordered services (ordered by a doctor, for example) and to the applicable rules and regulations of a third party payment provider.

Figure 6:
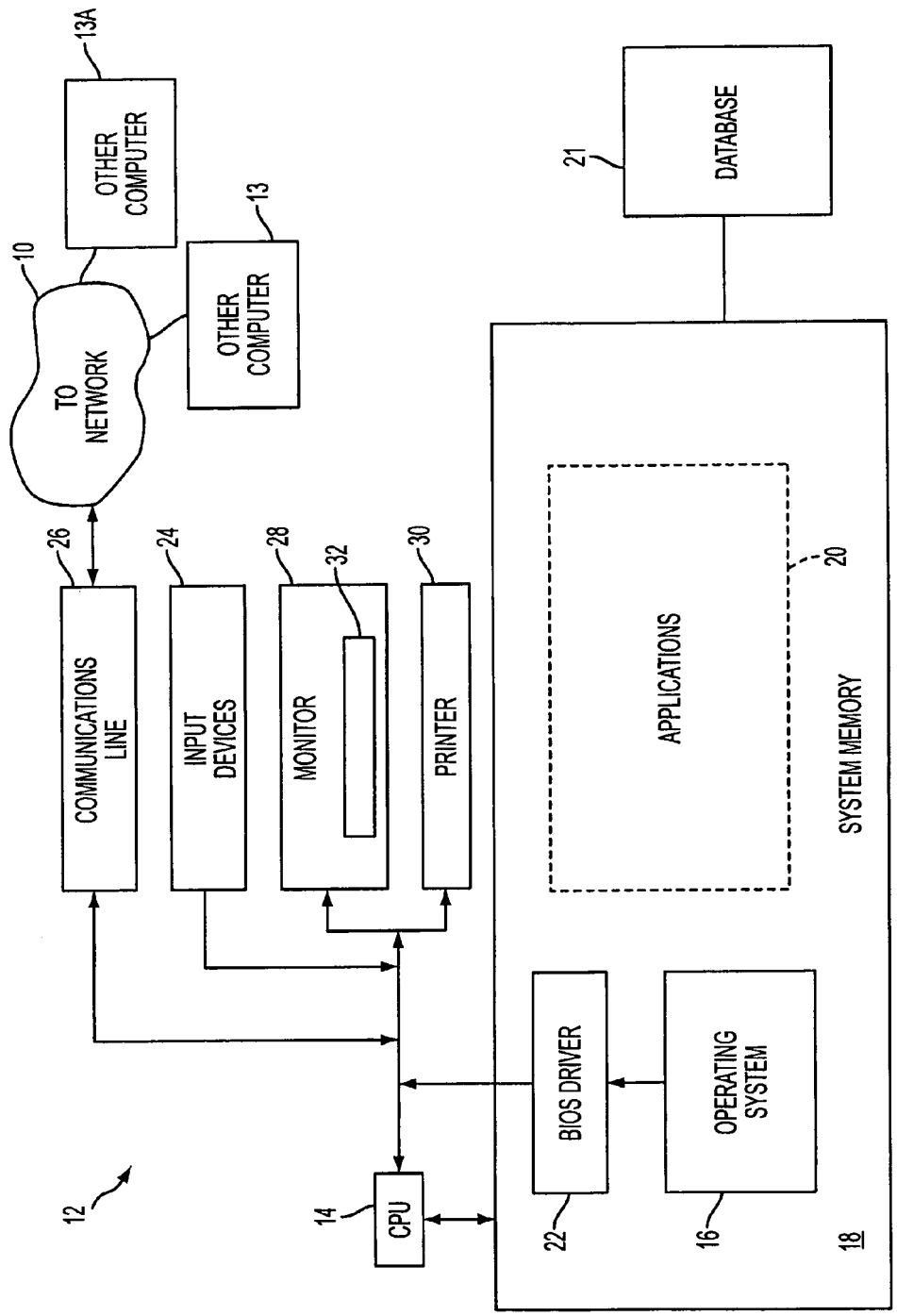
FIG. 6 is a diagram of a generic computing system, connected to a network, that may be used in certain embodiments of the present invention.

FIG. 6 illustrates the components of a generic computing system connected to a general purpose electronic network 10, such as a computer network. The computer network can be a virtual private network or a public network, such as the Internet. As shown in FIG. 6, the computer system 12 includes a central processing unit (CPU) 14 connected to a system memory 18. The system memory 18 typically contains an operating system 16, a BIOS driver 22, and application programs 20. In addition, the computer system 12 contains input devices 24 such as a mouse or a keyboard 32, and output devices such as a printer 30 and a display monitor 28, and a permanent data store, such as a database 21. The computer system generally includes a communications interface 26, such as an ethernet card, to communicate to the electronic network 10. Other computer systems 13 and 13A also connect to the electronic network 10 which can be implemented as a Wide Area Network (WAN) or as an internetwork, such as the Internet. In certain embodiments, such a computer system 12 can be used to implement the laboratory computing system 100 including the billing analysis software (which implements, for example, the logic discussed with respect to FIGS. 3 and 4) and/or the computing system 120 which contains the hospital, laboratory, patient, and billing data.

One skilled in the art would recognize that the foregoing describes a typical computer system 12 connected to an electronic network 10. It should be appreciated that many other similar configurations are within the abilities of one skilled in the art and it is contemplated that all of these configurations could be used with the methods and systems of the present invention. Furthermore, it should be appreciated that it is within the abilities of one skilled in the art to program and configure a networked computer system to implement the method steps of certain embodiments of the present invention, discussed further herein.

In certain embodiments, the present invention also contemplates providing computer readable data storage means with program code recorded thereon (i.e., software) for implementing the method steps described herein. In certain embodiments, the present invention also contemplates the transmission of data signals having information embodied thereon which includes the results of the billing analysis as described earlier herein.

Other embodiments of the invention will be apparent to those skilled in the art from a consideration of the specification and the practice of the invention disclosed herein. It is intended that the specification be considered as exemplary only, with such other embodiments also being considered as a part of the invention in light of the specification and the features of the invention disclosed herein. Furthermore, it should be recognized that the present invention includes the methods disclosed herein together with the software and systems used to implement the methods disclosed here.

What is claimed is:

1. A computer implemented method of analyzing third party payments for provider services, comprising the steps of:

processing, by a computing system, third party payment information data;

processing, by the computing system, provider services billing data provided to the third party to request payment;

automatically validating, by the computing system, provider services billing data against other provider services data including verifying that all billed services indicated in the billing data match actual services performed indicated in the other provider services data;

determining, by the computing system, whether any discrepancies exist between the third party payment information data, the provider services billing data, and the other provider services data;

generating, by the computing system based on an output of the determining step, a report listing discrepancies between the third party payment information data, the provider services billing data, and the other provider services data; and outputting, by the computing system, the report for review by at least one person.

2. The computer implemented method according to claim 1, wherein the step of automatically validating further comprises validating the provider services billing data against external data related to the provider services.

3. The computer implemented method according to claim 1, wherein the step of automatically validating comprises validating, for a particular patient encounter, a date of service between the third party payment information data, the provider services billing data, and the other provider services data.

4. The computer implemented method according to claim 1, wherein the third party payment information data comprises Medicare payment information data and wherein the other provider services data comprises laboratory services data.

5. The computer implemented method according to claim 4, wherein the step of automatically validating provider services billing data further comprises, for a patient encounter, validating existence of a doctor's order for each service billed in the billing data and validating a test description in the doctor's order for each laboratory service indicated in the laboratory services data.

6. The computer implemented method according to claim 5, wherein the step of automatically validating comprises accessing third party provided data to validate particular tests indicated in the laboratory services data with other tests indicated in the laboratory services data.

7. The computer implemented method according to claim 2, wherein the step of automatically validating comprises validating provider services billing data against billing rates for the provider services specified by the third party provided data for the provider services, and wherein the automatically validating step further comprises:

verifying that a date in which the provider services was performed matches a date provided on the provider services billing data;

verifying that a laboratory test described in the other provider services data matches an actual laboratory test performed; and verifying if any test codes corresponding to tests performed on a particular patient that are not covered for the particular patient are included in the provider services billing data.

8. The computer implemented method according to claim 7, wherein the step of automatically validating comprises validating provider services billing data for a group of billed services to detect duplicate billing of component services that are included in the billing data for the group of billed services.

9. The computer implemented method according to claim 1, wherein the step of processing the third party payment information data and the step of processing provider services billing data each comprise randomly selecting corresponding records including one or more patient encounter data.

10. The computer implemented method according to claim 2, wherein the step of generating a report listing discrepancies comprises tracking and classifying discrepancies across multiple reports.

11. The computer implemented method according to claim 10, wherein the step of generating a report listing discrepancies comprises generating an alert when discrepancies across multiple reports cross a certain threshold.

12. A system for analyzing third party payments for provider services, comprising:

an input unit that processes third party payment information data and provider services billing data provided to the third party to request payment;

a validation unit, connected to the input unit, that determines whether any discrepancies exist between the third party payment information data, other provider services billing data, and the provider services billing data so as to validate the provider services billing data against the third party payment information data and the other provider services data including verifying that all billed services indicated in the billing data match actual services performed indicated in the other provider services data; and a report unit that is connected to the validation unit and that generates and outputs a report listing discrepancies between the third party payment information data, the provider services billing data, and the other provider services data, wherein the validation unit further validates the provider services billing data against external data related to the provider services, and wherein the input unit randomly selects corresponding records from the third party payment information data and provider services billing data that include the same one or more patient encounter data.

13. A computer readable medium having program code recorded thereon that, when executed on a computing system, analyzes third party payments for provider services, the program code, when executed by the computing system, causing the computing system to perform the steps of:

processing third party payment information data;

processing provider services billing data provided to the third party to request payment;

determining whether any discrepancies exist between the third party payment information data, the provider services billing data, and other provider services data;

automatically validating, on the computing system based on an output of the determining step, provider services billing data against the other provider services data including verifying that all billed services indicated in the billing data match actual services performed indicated in the other provider services data;

generating a report listing discrepancies between the third party payment information data, the provider services billing data, and the other provider services data; and outputting the report for review by at least one person.

14. The computer implemented method according to claim 1, further comprising:

when any of the discrepancies listed in the report correspond to a predetermined type of discrepancy, outputting at least one of an e-mail and a voice alert to the at least one person.

15. A system for analyzing third party payments for provider services, comprising:

for analyzing third party payments for provider services, comprising:

an input unit that processes third party payment information data and provider services billing data provided to the third party to request payment;

a validation unit, connected to the input unit, that determines whether any discrepancies exist between the third party payment information data, other provider services billing data, and the provider services billing data so as to validate the provider services billing data against the third party payment information data and the other provider services data including verifying that all billed services indicated in the billing data match actual services performed indicated in the other provider services data;

a report unit that is connected to the validation unit and that generates and outputs a report listing discrepancies between the third party payment information data, the provider services billing data, and the other provider services data; and an alerting unit configured to output at least one of an e-mail and a voice alert to the at least one person when any of the discrepancies listed in the report generated by the report unit correspond to a predetermined type of discrepancy.

16. The computer implemented method according to claim 9, wherein the step of randomly selecting corresponding records includes the substeps of:

a) receiving user input with respect to random sampling by at least one of: (1) Current Procedural Terminology (CPT) code, (2) International Classification of Diseases (ICD-9) code, and (3) Physician identification code; and b) performing the random sampling based on the received user input.

17. A system for analyzing third party payments for provider services, comprising:

for analyzing third party payments for provider services, comprising:

an input unit that processes third party payment information data and provider services billing data provided to the third party to request payment;

a validation unit, connected to the input unit, that determines whether any discrepancies exist between the third party payment information data, other provider services billing data, and the provider services billing data so as to validate the provider services billing data against the third party payment information data and the other provider services data including verifying that all billed services indicated in the billing data match actual services performed indicated in the other provider services data;

a report unit that is connected to the validation unit and that generates and outputs a report listing discrepancies between the third party payment information data, the provider services billing data, and the other provider services data; and a user input unit configured to receive a user input with respect to random sampling by at least one of: (1) Current Procedural Terminology (CPT) code, (2) International Classification of Diseases (ICD-9) code, and (3) Physician identification code; and wherein the validation unit performs the random sampling based on the user input and based on randomly selecting corresponding records including one or more patient encounter data.

* * * * *